United States Patent [19]

Kanamaru et al.

[11] Patent Number: 4,910,013

[45] Date of Patent: Mar. 20, 1990

[54] HAIRDRESSING COMPOSITION

[75] Inventors: Tae Kanamaru, Tokyo; Hiroshi Ando, Chiba, both of Japan

[73] Assignee: KAO Corporation, Tokyo, Japan

[21] Appl. No.: 259,657

[22] Filed: Oct. 19, 1988

[30] Foreign Application Priority Data

Oct. 19, 1987 [JP] Japan ................ 263117/87

[51] Int. Cl.$^4$ .............................. A61K 7/11
[52] U.S. Cl. .......................... 424/47; 424/70
[58] Field of Search .................... 424/47, 70

[56] References Cited

U.S. PATENT DOCUMENTS 4,751,074  6/1988  Matsunaga et al. ............ 424/70

FOREIGN PATENT DOCUMENTS

| 0155806 | 9/1985 | European Pat. Off. . |
| 0181547 | 5/1986 | European Pat. Off. . |
| 0120788 | 9/1981 | Japan ................ 424/47 |
| 0032812 | 2/1983 | Japan ................ 424/47 |
| 2066659 | 7/1981 | United Kingdom . |
| 2102288 | 2/1983 | United Kingdom . |

Primary Examiner—Ellis P. Robinson
Assistant Examiner—P. L. Prater
Attorney, Agent, or Firm—Sughrue, Mion, Zinn, Macpeak & Seas

[57] ABSTRACT

A hairdressing composition which comprises:
(A) one or more branched alkyl quaternary ammonium salt, and
(B) one or more silicone compounds is disclosed. This hairdressing composition is excellent in smoothness and flexibility, exhibits only a little oily and stickiness and has a high antistatic effect.

5 Claims, No Drawings

HAIRDRESSING COMPOSITION

FIELD OF THE INVENTION

This invention relates to a novel hairdressing composition. More particularly, it relates to a hairdressing composition in the form of, for example, a hair rinse, a hair conditioner, a hair treatment, a styling mousse, a styling lotion, a hair spray, a brushing aid or a styling gel which comprises a branched alkyl quaternary ammonium salt and a silicone compound. The hairdressing composition is excellent in smoothness and flexibility, exhibits only a little oily feel and stickiness and has a high antistatic effect.

BACKGROUND OF THE INVENTION

Conventional hair-care products, such as hair rinses to be used during shampooing, and a styling air or a brushing aid to be used in styling the hair, comprise a straight-chain alkyl quaternary ammonium salt, such as distearyldimethyl-ammonium chloride, in order to make the hair flexible while preventing static electrification so a to facilitate the treatment of the hair. However, none of these straight-chain alkyl quaternary ammonium salts can impart a sufficient flexibility and smoothness to the hair when employed alone. Thus, they are generally combined with various oils such as higher alcohols, glyceride, liquid paraffin or esters. However, it is unavoidable that the use of these oils causes a disadvantage, namely an oily and sticky feel.

On the other hand, silicone compounds, which are superior in smoothness to higher alcohols, glyceride, liquid paraffin and esters, have been widely applied to a number of hairdressing compositions. However, they are also accompanied by an oily and sticky feel.

Therefore, it has been attempted to combine a silicone compound with a straight-chain alkyl quaternary ammonium salt to thereby give a hairdressing composition which is excellent in smoothness and flexibility and has a high antistatic effect. For example, JP-A-No. 58-4709 (The term "JP-A" as used herein means an "unexamined published Japanese patent application") teaches a brushing aid composition which comprises a specific long-chain alkyl quaternary ammonium salt and a specific cyclic silicone compound, and which prevents static electricity caused by the brushing and shows scarcely any stickiness. Further, JP-A- No. 56-99407 (corresponding to U.S. Pat. No. 4,493,824) discloses a hair rinse composition which comprises a specific quaternary ammonium salt, a specific silicone compound and polyethylene glycol. However, each of these products is unsatisfactory since they give an oily and sticky feel.

Thus, heretofore, it is unavoidable that a hairdressing composition which is excellent in smoothness and flexibility would show an intense oily feel.

Further, JP-A- No. 61-267505 (corresponding to U.S. Pat. No. 4,711,776) discloses a hairdressing composition containing a branched alkyl quaternary ammonium salt and ordinary fats or fatty oils. However, these products are unsatisfactory in providing smoothness, conditioning property and NON-oily feel at the same time. Moreover, since they are accompanied by an intense oily feel, a hairdressing composition such as a styling aid, a styling mousse, etc, have a good NON-Oily and NON-sticker feel can be hardly obtained.

SUMMARY OF THE INVENTION

Under these circumstances, the present inventors have conducted extensive studies in order to overcome these problems. As a result, it has been found in the present invention that a hairdressing composition which is excellent in smoothness and flexibility, shows only a little oily feel and has a high antistatic effect without any stickiness can be obtained by combining a silicone compound with a branched alkyl quaternary ammonium salt.

Accordingly, the present invention provides a hairdressing composition which comprises:

(A) one or more branched alkyl quaternary ammonium salt represented by the general formula (I):

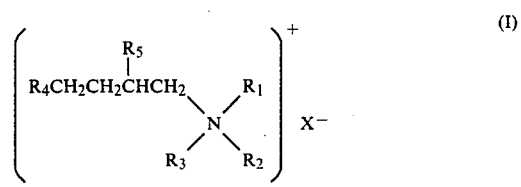

wherein $R_1$ and $R_2$ each represents a benzyl group, an alkyl group having 1 to 3 carbon atoms or a hydroxyalkyl group having 1 to 3 carbon atoms; $R_3$ represents a group of the formula

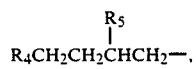

wherein $R_4$ and $R_5$ are as defined below, or an alkyl group having 1 to 3 carbon atoms; $R_4$ and $R_5$ each represents an alkyl group having 2 to 16 carbon atoms; and $X^-$ represents a halogen ion or an organic anion, and (B) one or more silicone compound selected from the group consisting of dimethyl polysiloxane, methylphenyl polysiloxane, amino-denatured silicone, fatty aciddenatured polysiloxanes, alcohol-denatured silicones, aliphatic alcohol-denatured polysiloxanes, polyetherdenatured silicones, epoxy-denatured silicones, fluorinedenatured silicones, cyclic silicones and alkyl-denatured silicones.

DETAILED DESCRIPTION OF THE INVENTION

The branched alkyl quaternary ammonium salt of component (A) represented by formula (I) in the hairdressing composition according to the present invention may be synthesized from a Guerbet alcohol having 8 to 36 carbon atoms

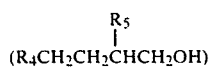

as described, for example, in JP-A-No. 61-15865. Preferable examples of this branched alkyl quaternary ammonium salt include monoalkyl quaternary ammonium salts such as alkyltrimethylammonium salts, alkyldimethylhydroxyethylammonium salts and alkyldimethylbenzylammonium salt each having an alkyl group derived from a Guerbet alcohol, dialkyldimethylammonium salts, dialkylmethylhydroxyethylammonium salts, and dialkylmethylbenzylammonium salts. Examples of the counter ion of these ammonium salts include halogen ions such as chlorine, iodine and bromine ions, and organic anions such as methosulfate, ethosulfate, methophosphate and ethophosphate. Examples of the alkyl group derived from a Guerbet alcohol include 2-hexyldecyl, 2-octyldodecyl, 2-decyltetradecyl and 2-dodecylhexadecyl groups. Particularly preferable examples of the branched alkyl quaternary ammonium salt (I) include 2-octyldodecyltrimethylammonium chloride, 2-decyltetradecyltrimethylammonium chloride, 2-dodecylhexadecyltrimethylammonium chloride, di-2-hexyldecyldimethylammonium chloride and di-2-octyldodecylammonium chloride. Either one of these branched alkyl quaternary ammonium salts or a mixture thereof may be used in the present invention. The total content of component (A) may range from 0.01 to 20% (by weight, the same will apply hereinafter), preferably 0.1 to 10%, based on the total weight of the hairdressing composition.

Examples of the silicone compound of component (B) are as follows:

(1) dimethyl polysiloxane:

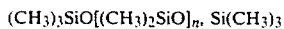

$$(CH_3)_3SiO[(CH_3)_2SiO]_{n'}Si(CH_3)_3 \quad (II)$$

wherein $n'$ is from 0 to 9,000, (2) methylphenyl polysiloxane:

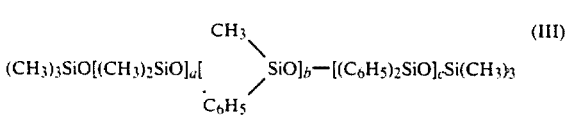

$$(CH_3)_3SiO[(CH_3)_2SiO]_a[\underset{C_6H_5}{\overset{CH_3}{SiO}}]_b-[(C_6H_5)_2SiO]_cSi(CH_3)_3 \quad (III)$$

wherein $a+b+c$ is 1 to 550 provided that when b is 0, c is not 0 and when c is 0, b is not 0, (3) amino-denatured silicone:

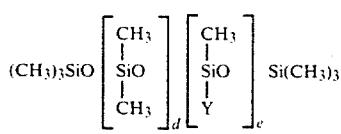

wherein d is 0 to 100, e is 1 to 50, and Y represents an alkyl group of the formula (a)

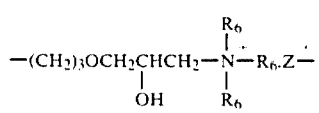

or the formula (b)

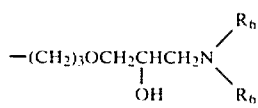

wherein $R_6$ represents an alkyl group having 1 to 3 carbon atoms and Z represents a Cl, Br or I atom, (4) fatty acid-denatured polysiloxane:

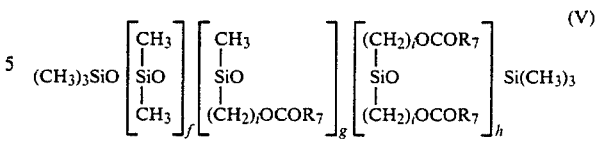

wherein f, g and h each represents 1 to 350, i is 0 to 10, and $R_7$ represents a group $C_{n_1}H_{2n_1+1}$, in which $n_1$ is 9 to 21, (5) alcohol-denatured silicone:

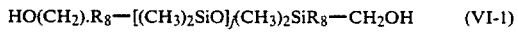

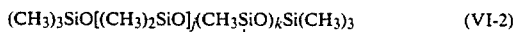

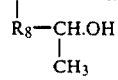

wherein j and k each represents 1 to 500, preferably 1 to 200; and $R_8$ represents a group $C_{n_2}H_{2n_2}$, in which $n_2$ is 0 to 4, (6) aliphatic alcohol-denatured polysiloxane:

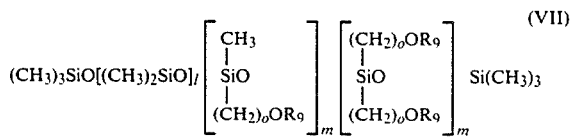

wherein $l+m+n$ is 1 to 300, o is 0 to 5, and $R_9$ represents a group $C_{n_3}H_{n_3+1}$, in which $n_3$ is 4 to 22.

(7) polyether-denatured silicone:

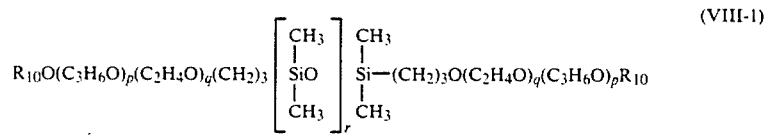

wherein p is 0 to 35, q is 1 to 45, r is 0 to 400, and $R_{10}$ represents a group $C_nH_{2n+1}$, in which n is 1 to 4,

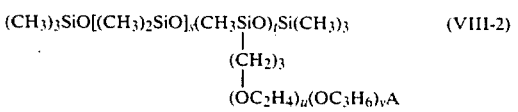

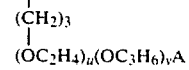

wherein s is 1 to 100, preferably 20 to 80; t is 1 to 50, preferably 3 to 30; u is 0 to 50, preferably 5 to 30; v is 0 to 50, preferably 0 to 35; and A is an alkyl group having 1 to 12 carbon atoms or a group $OC_{n_4}H_{2n_4+1}$, in which $n_4$ is 0 to 6, (8) epoxy-denatured silicone:

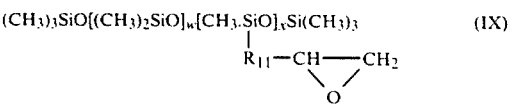

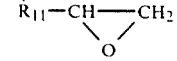

wherein w is 1 to 500, preferably 1 to 250; x is 1 to 50, preferably 1 to 30; and $R_{11}$ represents an alkylene group having 1 to 3 carbon atoms, (9) fluorine-denatured silicone:

$$(CH_3)_3SiO(CH_3SiO)_ySi(CH_3)_3 \qquad (X)$$
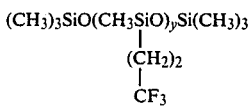

wherein y is 1 to 400, preferably 1 to 250,
(10) cyclic silicone:

$$\left[ \begin{array}{c} R_{12} \\ | \\ SiO \\ | \\ R_{12} \end{array} \right]_z \quad (XI)$$
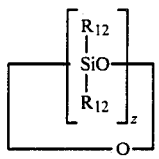

wherein z is 3 to 8, and $R_{12}$ represents an alkyl group having 1 to 3 carbon atoms, and
(11) alkyl-denatured silicone:

$$(CH_3)_3SiO(CH_3SiO)_\alpha(CH_3SiO)_\beta Si(CH_3)_3 \qquad (XII\text{-}1)$$
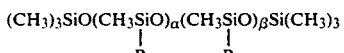

with $R_{13}$ and $R_{14}$ substituents
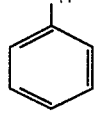

wherein $\alpha$ and $\beta$ each represents 1 to 500, preferably 1 to 200; $R_{13}$ represents an alkyl group having 2 to 18 carbon atoms; and $R_{14}$ is a group $C_{n_5}H_{2n_5}$, in which $n_5$ is 0 to 4, $$(CH_3)_3SiO[(CH_3)_2SiO]_r(CH_3SiO)_\omega Si(CH_3)_3 \qquad (XII\text{-}2)$$
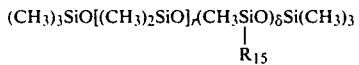

wherein r and $\omega$ each represents 1 to 500, preferably 1 to 200; and $R_{15}$ represents an alkyl group having 10 to 16 carbon atoms.

Among these silicone compounds, those as defined in the above (1), (3), (7) and (10) are preferably employed in a hairdressing composition to be rinsed away, for example, a hair rinse or a hair conditioner. Regarding the silicone compounds of (1), the n' in the formula (II) may range from 0 to 9,000, though it preferably ranges from 100 to 1,000 in order to give a hair style of a light feel. On the other hand, those as defined in the above (1), (2), (3), (7) and (10) are preferably employed in a hairdressing composition which is not rinsed away, such as a hair cream, a styling lotion or a styling mousse. Regarding the silicone compounds of (1), the n' in the formula (II) preferably range from 6,000 to 8,000 in order to minimize any oily feel.

It is preferable that the total content of component (B) ranges from 0.01 to 20%, more preferably 0.1 to 10%, based on the total weight of the hairdressing composition.

The hairdressing composition of the present invention may further contain various components selected from among, for example, higher alcohols having straight-chain or branched alkyl or alkenyl group(s), fats and oils such as lanolin and derivatives thereof, esters, liquid paraffin, higher fatty acids and long-chain amideamines having alkyl or alkenyl group(s), medical components such as an antidandruff agent and vitamins, preservatives such as parabens, thickners such as water soluble polymers, colorants such as dyes and pigments, conditioning agents such as cationized polymers, pearlings such as glycol esters, hair styling polymers such as acryl resin solutions and various perfume compositions, if required.

The hairdressing composition according to the present invention can be produced, for example, by the following procedure.

Component (A) and component (B), if desired, the other fats and oils, are mixed while heating at 40 to 80° C. to prepare a composition I. Separately, a water-soluble component is uniformly dissolved in water while heating at 40 to 80° C. to prepare a composition II. The obtained composition II is gradually added to the obtained composition I under stirring. After cooling to room temperature (15 to 25° C.), a component having a low heat-stability such as a lower alcohol, a perfume, etc, is added thereto to obtain a hairdressing composition as a desired product. If requested, it may be filled into a pressure vessel together with a propellants.

Table 1 below shows the particularly preferable ranges of the components, including the optional ones, of the hairdressing composition of the present invention.

TABLE 1

| Component | Hair Rinse, Hair Conditioner (wt %) | Hair Cream, Treatment (wt %) | Styling Lotion, Styling Mousse, Hair Spray, Styling Gel (wt %) |
|---|---|---|---|
| Branched alkyl quaternary ammonium salt (Component (A)) | 0.1~10 | 0.1~10 | 0.1~10 |
| Silicone compound (Component (B)) | 0.1~10.0 | 0.1~10.0 | 0.1~10.0 |
| Surfactant other than (A) | 0~5 | 0~10 | 0~5 |
| Fat or oil other than (B) | 0~10 | 0~20 | 0~10 |
| Resin | 0~1 | 0~5 | 0.3~10.0 |
| Water | 60~99.8 | 40~99.8 | 0~96.5 |
| Volatile solvent (e.g., ethanol) | 0~20 | 0~20 | 3~99.5 |
| Other components | 0~20 | 0~20 | 0~20 |

When the hairdressing composition of the present invention is in the form of an aerosol, such as a hair mousse or hair spray, it is preferable that a propellant, such as a fluorocarbon, liquefied petroleum gas or dimethyl ether, is added to a stock solution of the above composition in such an amount as to give an inner pressure of 2.0 to 6.0 kg/cm². G, i.e., from 1 to 20% based on the total composition.

The hairdressing composition of the present invention shows little oily feel and is excellent in smoothness, flexibility and antistatic effect.

The present invention is now illustrated in greater detail with reference to Examples, but it should be understood that the present invention is not deemed to be limited thereto. In these Examples, each evaluation was conducted in the following manners.

(1) Organoleptic evaluation 20 g (length: 15 cm) of the hair of Japanese women, who had never received a perm nor bleached their hair, was bundled. In the case of a hairdressing composition to be rinsed away, 2 g of the hairdressing composition was uniformly applied to the hair bundle which was then rinsed with running water for 30 sec. and dried with a towel and then with a drier. In the case of a hairdressing composition not to be rinsed away, a definite amount of the hairdressing composition was applied to the hair bundle which was then air-dried. The flexibility, smoothness and oily feel of the hair bundle were organoleptically evaluated by ten experienced panelists according to the following criterion.

Each evaluation score is the mean of these panelists.

Criterion

+2: very good,
+1: good,
0: moderate,
−1: poor, and
−2: very poor.

(2) Combing load

A hair bundle was treated in the same manner as the one described in (1) above and dried with a towel. The moist hair bundle, which contained approximately 0.7 g/g of moist hair, was combed with a strain gauge, either as such or after drying with a drier, to thereby determine the combing load. The determination was repeated 20 times in a thermostat chamber at 20° C. under a relative humidity of 65% and the mean (g) was referred to as the combing value.

(3) Static electrification

The dried hair bundle described above was combed ten times in a thermostat chamber at 20° C. under a relative humidity of 65% and the static electricity (kV) thus induced was determined.

EXAMPLE 1

A hair rinse of the composition as shown in Table 2 below was prepared and the rinsing properties thereof were evaluated.

Preparation

One or two of components (1), (2) and (3), and component (4) were uniformly dispersed in components (5) and heated. The resulting dispersion was added to a heated component (6) under stirring to obtain a hair rinse.

The results are shown in Table 2 below.

TABLE 2

| Component (%) | Comparison 1 | Comparison 2 | Comparison 3 | Invention 1 |
|---|---|---|---|---|
| (1) 2-octyldodecyltrimethylammonium chloride (Component A) | — | — | 1.0 | 1.0 |
| (2) Dicetostearyldimethyl ammonium chloride | 1.0 | 1.0 | — | — |
| (3) Dimethyl polysiloxane (Component B) (in formula (II), n' = 225 (average)) | — | 1.0 | — | 1.0 |
| (4) Cetyl alcohol | 2.0 | 2.0 | 2.0 | 2.0 |
| (5) Propylene glycol | 5.0 | 5.0 | 5.0 | 5.0 |
| (6) Water | 92.0 | 91.0 | 92.0 | 91.0 |
| Effect on hair | | | | |
| Organoleptic evaluation: | | | | |
| Nonoily feel | −1.0 | −1.2 | +0.5 | +1.9 |
| Smoothness | 0 | +0.6 | +0.3 | +1.8 |
| Flexibility | 0 | +0.2 | +0.8 | +1.8 |
| Combing load (g): | | | | |

TABLE 2-continued

| Component (%) | Comparison 1 | Comparison 2 | Comparison 3 | Invention 1 |
|---|---|---|---|---|
| Moist | 220 | 210 | 196 | 150 |
| Dry | 145 | 85 | 71 | 62 |
| Static electrification (kV): | 1.9 | 1.7 | 1.5 | 0.8 |

As shown in Table 2, the hair rinse composition of Invention 1 was excellent in smoothness and antistatic properties, showed only a little oily feel and had an excellent texture.

EXAMPLE 2

A hair rinse of the following composition was prepared and the rinsing properties thereof were evaluated by twenty female panelists by a pair-test wherein +2 represents very good while +1 represents good.

The results are shown in Table 3 below.

| | Amount (%) |
|---|---|
| Product of Invention 2 | |
| (1) 2-decyltetradecyltrimethylammonium chloride | 1.0 |
| (2) Polyether-denatured silicone (in formula (VIII-2), S = 50, t = 10, u = v = 20, A = OH) | 1.0 |
| (3) Propylene glycol | 5.0 |
| (4) Hydroxyethylcellulose | 0.5 |
| (5) Water | 92.1 |
| (6) Perfume | 0.4 |
| Comparative Product 4 (Comparison 4) | |
| (1) Dicetyldimethylammonium chloride | 1.0 |
| (2) Polyether-denatured silicone (in formula (VIII-2), s = 50, t = 10, u = v = 20, A = OH) | 1.0 |
| (3) Propylene glycol | 5.0 |
| (4) Hydroxyethylcellulose | 0.5 |
| (5) Water | 92.1 |
| (6) Perfume | 0.4 |

TABLE 3

| | Comparison 4 | | | Invention 2 | |
|---|---|---|---|---|---|
| Effect on Hair | +2 | +1 | 0 | +1 | +2 |
| 1. Total evaluation | 0 | 1 | 7 | 10 | 2 |
| 2. Finger-combing at rinsing | 0 | 1 | 7 | 9 | 1 |
| 3. Flexibility at rinsing | 0 | 1 | 7 | 9 | 2 |
| 4. Monoily feel after drying | 0 | 1 | 8 | 7 | 3 |
| 5. Smoothness after drying | 0 | 0 | 9 | 7 | 3 |
| 6. Combing after drying | 0 | 1 | 8 | 9 | 1 |

EXAMPLE 3

| Hair Treatment Composition (Product of Invention 3) | Amount (%) |
|---|---|
| (1) 2-dodecylhexadecyltrimethylammonium chloride | 1.5 |
| (2) Monostearyltrimethylammonium chloride | 1.0 |
| (3) Cyclic silicone (in formula (XI), z = 5, $R_{12}$ = $CH_3$) | 2.0 |
| (4) Dimethyl polysiloxane (in formula (II), n' = 1,000) | 0.2 |
| (5) Cetostearyl alcohol | 1.0 |
| (6) Lanolin | 3.0 |
| (7) Liquid paraffin | 3.0 |
| (8) Polypeptide (hydrolyzate of collagen) | 5.0 |
| (9) Cationized cellulose | 3.0 |
| (10) Polyoxyethylene oleyl ether (EO = 5) | 0.5 |
| (11) Methyl paraben | 0.2 |
| (12) Perfume | 0.4 |
| (13) Water | balance |

-continued

| Hair Treatment Composition (Product of Invention 3) | Amount (%) |
|---|---|
| Total: | 100.0% |

Preparation

Components (8), (9) and (11) were uniformly dispersed in component (13) and heated. A uniform dispersion of components (1), (2), (3), (4), (5), (6), (7) and (10) was heated and added thereto under stirring. After cooling, component (12) was blended therewith. Thus, a hair treatment composition was obtained which was excellent in smoothness and antistatic properties, showed only a little oily feel and had an excellent texture.

EXAMPLE 4

| Hair cream compositions (Product of Invention 4) | Amount (%) |
|---|---|
| (1) 2-decyltetradecyltrimethylammonium chloride | 2.0 |
| (2) Cetyltrimethylammonium chloride | 1.0 |
| (3) Polyoxyethylene sorbitan monostearate (EO = 20) | 0.5 |
| (4) Cetyl alcohol | 5.0 |
| (5) Dipropylene glycol | 6.0 |
| (6) Glycerol | 10.0 |
| (7) Liquid paraffin | 3.0 |
| (8) Amino-denatured silicone[1]* | 2.0 |
| (9) Perfume | 0.4 |
| (10) Water | balance |
| Total | 100.0% |

[1]*In formula (IV), d = 3, e = 2, Y = $-(CH_2)_3OCH_2\underset{\underset{OH}{|}}{CH}CH_2N(C_2H_5)_2$.

Preparation

Component (10) was heated and a homogeneous dispersion of components (1), (2), (3), (4), (5), (6), (7) and (8) was added thereto. After cooling, component (9) was blended therewith. Thus, a hair cream composition was obtained which was excellent in smoothness and flexibility, showed little stickiness and had an excellent texture.

EXAMPLE 5

| Conditioning mousse composition (Product of Invention 5) | Amount (%) |
|---|---|
| (1) 2-hexyldecyltrimethylammonium chloride | 0.5 |
| (2) Octyldodecyl myristate | 1.0 |
| (3) Dipropylene glycol | 1.0 |
| (4) Methylphenyl polysiloxane[2]* | 1.0 |
| (5) Glycerol | 2.5 |
| (6) Liquid paraffin | 2.5 |
| (7) Polyoxyethylene sorbitan monostearate | 0.2 |
| (8) Alcohol | 5.0 |
| (9) Methyl paraben | 0.1 |
| (10) Perfume | 0.1 |

-continued

| Conditioning mousse composition (Product of Invention 5) | Amount (%) |
|---|---|
| (11) Propellant (LPG) | 10.0 |
| (12) Water | Balance |
| Total | 100.0% |

[2]*In formula (III), a = 190, b = 0, c = 10.

Preparation

Component (9) was added to component (12) and heated. A uniform dispersion of components (1), (2), (3), (4), (5), (6) and (7) was heated and added thereto under stirring. After cooling, components (8) and (10) were blended therewith. The resulting composition was filled in an aerosol can and propellant (11) was added thereto. Thus, a conditioning mousse composition having an excellent texture was obtained.

EXAMPLE 6

| Styling lotion composition (Product of Invention 6) | Amount (%) |
|---|---|
| (1) 2-decyltetradecyltrimethylammonium chloride | 0.5 |
| (2) Dimethyl polysiloxane (in formula (II), n' = 7,000 (average)) | 1.5 |
| (3) Polyether-denatured silicone (in formula (VIII-2), s = 70, t = 6, u = 20, v = 30, A = OCH$_3$) | 0.5 |
| (4) Acryl resin | 1.0 |
| (5) Ethanol | 30.0 |
| (6) Perfume | 0.1 |
| (7) Water | balance |
| Total | 100.0% |

Preparation

Components (1), (2), (3), (5) and (6) and a portion of component (7) were emulsified in a homomixer and then component (4) and the balance of component (7) were added thereto. Thus, a styling lotion composition was obtained which was excellent in smoothness and flexibility, showed only a little oily feel and had a high antistatic effect and an excellent styling effect.

EXAMPLE 7

Brushing air compositions as shown in Table 4 below were prepared and evaluated. Table 4 shows the results.

Each brushing aid composition was prepared by adding to components (1), (2), (3), (4), (5) and (7) to component (6), stirring the obtained mixture and then filling the same into an aerosol can together with propellants (8) and (9).

As shown in Table 4 below, each product of the present invention had a significantly small combing load and static electrification, an excellent flexibility and smoothness in the organoleptic evaluation and only a little oily feel, compared with the comparative compositions.

TABLE 4

| Component | Comp. 5 (%) | Comp. 6 (%) | Comp. 7 (%) | Comp. 8 (%) | Comp. 9 (%) | Comp. 10 (%) | Invention 7 (%) | Invention 8 (%) |
|---|---|---|---|---|---|---|---|---|
| (1) 2-dodecylhexadecyl-trimethylammonium chloride | — | — | — | — | — | 0.2 | 0.2 | 0.2 |
| (2) Stearyltrimethyl-ammonium chloride | 0.2 | — | 0.2 | 0.2 | 0.2 | — | — | — |
| (3) Cyclic silicone | — | 3.0 | 3.0 | — | 3.0 | — | 3.0 | — |

TABLE 4-continued

| Component | Comp. 5 (%) | Comp. 6 (%) | Comp. 7 (%) | Comp. 8 (%) | Comp. 9 (%) | Comp. 10 (%) | Invention 7 (%) | Invention 8 (%) |
|---|---|---|---|---|---|---|---|---|
| (in formula (XI), z = 5, $R_{12}$ = $CH_3$) | | | | | | | | |
| (4) Dimethyl polysiloxane (in formula II, n' = 300) | — | — | — | 3.0 | — | — | — | 3.0 |
| (5) 2,2-dimethyl-1,3-propanediol | — | — | — | — | 1.0 | — | — | — |
| (6) Ethanol | Balance | Balance | Balance | Balance | Balance | Balance | Balance | Balance |
| (7) Perfume | 0.08 | 0.08 | 0.08 | 0.08 | 0.08 | 0.08 | 0.08 | 0.08 |
| (8) Freon 12 | 37.91 | 37.91 | 37.91 | 37.91 | 37.91 | 37.91 | 37.91 | 37.91 |
| (9) Freon 11 | 37.91 | 37.91 | 37.91 | 37.91 | 37.91 | 37.91 | 37.91 | 37.91 |
| Effect on hair | | | | | | | | |
| Organoleptic evaluation: | | | | | | | | |
| Non-oily feel | 0 | −1.0 | −1.0 | −1.2 | −1.2 | +0.2 | +1.7 | +1.5 |
| Flexibility | −0.1 | −0.5 | +0.1 | +0.2 | +0.2 | +0.3 | +1.6 | +1.8 |
| Smoothness | −0.4 | +0.3 | +0.5 | +0.8 | +0.9 | +0.5 | +1.8 | +1.9 |
| Combing load (g): | | | | | | | | |
| Dry | 180 | 165 | 158 | 150 | 150 | 168 | 95 | 88 |
| Static electrification (kV): | 3.5 | 4.0 | 2.8 | 2.0 | 1.8 | 2.9 | 0.4 | 0.5 |

EXAMPLE 8

| Styling gel composition (Product of Invention 9) | Amount (%) |
|---|---|
| (1) 2-hexyldecyltrimethylammonium chloride | 0.5 |
| (2) Polyether-denatured silicone (in formula (VIII-2), s = 25, t = 4, u = 10, v = 0, A = OH) | 1.0 |
| (3) Cationized cellulose (Polymer JR-400) | 2.0 |
| (4) Hydroxyethylcellulose | 0.5 |
| (5) Polyoxyethylene oleyl ether (EO = 5) | 0.3 |
| (6) Perfume | 0.15 |
| (7) Water | Balance |
| Total | 100.0% |

Preparation

Components (1), (3) and (4) were added to component (7) and the resulting mixture was heated and homogenized. After cooling, a mixture of components (2), (5) and (6) was added thereto and stirred. Thus, a styling gel composition was obtained which was excellent in smoothness and combing properties, showed only a little oily feel and had a high styling effect.

EXAMPLE 9

| Styling mousse composition (Product of Invention 10) | Amount (%) |
|---|---|
| (1) 2-dodecylhexadceyltrimethylammonium chloride | 0.5 |
| (2) Methylphenyl polysiloxane (in formula (III), a = 0, b = 50, c = 0) | 1.0 |
| (3) Polyether-denatured silicone (in formula (VIII-2), s = 60, t = 5, u = 15, v = 30, A = $OCH_3$) | 1.5 |
| (4) Plysize L53P*[3] | 8.0 |
| (5) Polyoxyethylene hexadecyl ether (EO = 10) | 0.5 |
| (6) Ethanol | 5.0 |
| (7) Perfume | 0.2 |
| (8) Colorant | 0.01 |
| (9) Water | Balance |
| (10) LPG (4.0 kg/$cm^2$.G, 20° C.) | 10.0 |

-continued

| Styling mousse composition (Product of Invention 10) | Amount (%) |
|---|---|
| Total | 100.0% |

[3]*manufactured by Goo Kagaku K.K.

Preparation

Components (1), (2), (3), (5), (6) and (7) and a portion of component (9) were emulsified in a homomixer. Then, component (8) dissolved in the balance of component (9) was added thereto and the resulting mixture was filled in an aerosol can together with propellant (10). Thus, a styling mousse composition was obtained which was excellent in combing properties, flexibility, and smoothness, showed only a little oily feel and had a high antistatic effect.

While the invention has been described in detail and with reference to specific embodiments thereof, it will be apparent to one skilled in the art that various changes and modifications can be made therein without departing from the spirit and scope thereof.

What is claimed is:

1. A hairdressing composition which comprises:
   (A) One or more branched alkyl quaternary ammonium salt represented by the general formula (I):

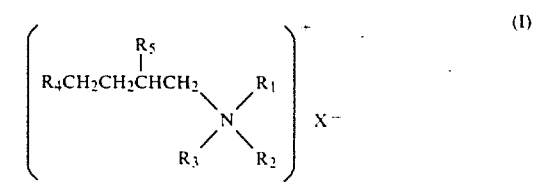

wherein $R_1$ and $R_2$ each represents a benzyl group, an alkyl group having 1 to 3 carbon atoms or a hydroxyalkyl group having 1 to 3 carbon atoms;

$R_3$ represents a group of the formula

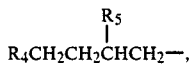

wherein
R$_4$ and R$_5$ are as defined below, or an alkyl group having 1 to 3 carbon atoms; R$_4$ and R$_5$ each represents an alkyl group having 2 to 16 carbon atoms; and X$^-$ represents a halogen ion or an organic anion, and (B) one or more silicones compound selected from the group consisting of dimethyl polysiloxane, methylphenyl polysiloxane, amino-denatured silicone, fatty aciddenatured polysiloxanes, alcohol-denatured silicones, aliphatic alcohol-denatured polysiloxanes, polyetherdenatured silicones, epoxy-denatured silicones, fluorinedenatured silicones, cyclic silicones and alkyl-denatured silicones.

2. The hairdressing composition as claimed in claim 1, which comprises 0.01 to 20% by weight of component (A) and 0.01 to 20% by weight of component (B), based on the total weight of the hairdressing composition.

3. The hairdressing composition as claimed in claim 1, wherein said branched alkyl quaternary ammonium salt is selected from the group consisting of monoalkyl quaternary ammonium salts, dialkyldimethylammonium salts, dialkylmethylhydroxyethylammonium salts and dialkylmethylbenzylammonium salts.

4. The hairdressing composition as claimed in claim 1, wherein said branched alkyl quaternary ammonium salt is selected from the group consisting of 2-octyldodecyltrimethylammonium chloride, 2-decyltetradecyltrimethylammonium chloride, 2-dodecylhexadecyltrimethylammonium chloride, di-2-hexyldecyldimethylammonium chloride and di-2-octyldodecylammonium chloride.

5. The hairdressing composition as claimed in claim 2, which comprises 0.1 to 10% by weight of component (A) and 0.1 to 10% by weight of component (B), based on the total weight of the hairdressing composition.

* * * * *